United States Patent [19]
Horan et al.

[11] Patent Number: 5,493,757
[45] Date of Patent: Feb. 27, 1996

[54] PROTECTIVE HANDLE AND ADAPTER FOR USE WITH A SURGICAL LIGHTING FIXTURE

[75] Inventors: Robert T. Horan, Northridge; Bruno J. Ramirez, Simi Valley, both of Calif.

[73] Assignee: Devon Industries, Inc., Chatsworth, Calif.

[21] Appl. No.: 246,340

[22] Filed: May 19, 1994

[51] Int. Cl.⁶ ............................ B25G 1/02; A47B 95/02
[52] U.S. Cl. ........................... 16/114 R; 16/111 R
[58] Field of Search ........................... 16/111 R, 114 R, 16/DIG. 12; 362/804

[56] References Cited

U.S. PATENT DOCUMENTS

| | | | |
|---|---|---|---|
| D. 298,864 | 12/1988 | Jefferson | D26/113 |
| 4,559,671 | 12/1985 | Andrews et al. | 16/111 R |
| 4,605,124 | 8/1986 | Sandel et al. | 16/114 R |
| 4,844,252 | 7/1989 | Barron et al. | 16/111 R |
| 4,974,288 | 12/1989 | Reasner | 16/111 R |
| 5,156,456 | 10/1989 | Hoftman et al. | 16/114 R |
| 5,273,157 | 12/1993 | Spina | 16/114 R |

Primary Examiner—Lowell A. Larson
Assistant Examiner—Donald M. Gurley
Attorney, Agent, or Firm—Poms, Smith, Lande & Rose

[57] ABSTRACT

A lighting fixture handle and adapter assembly for attaching a handle to a lighting fixture. The handle includes an elongate member and a shield having a central portion and two hinged side portions movable between a folded position and a use position in which the side portions are substantially aligned with the sides of the central portion. At least one of the handle and adapter includes a biasing element for biasing the shield in such a manner that side portions arranged in the folded position will be repositioned to the use position when the handle and the adapter are secured to one another.

17 Claims, 2 Drawing Sheets

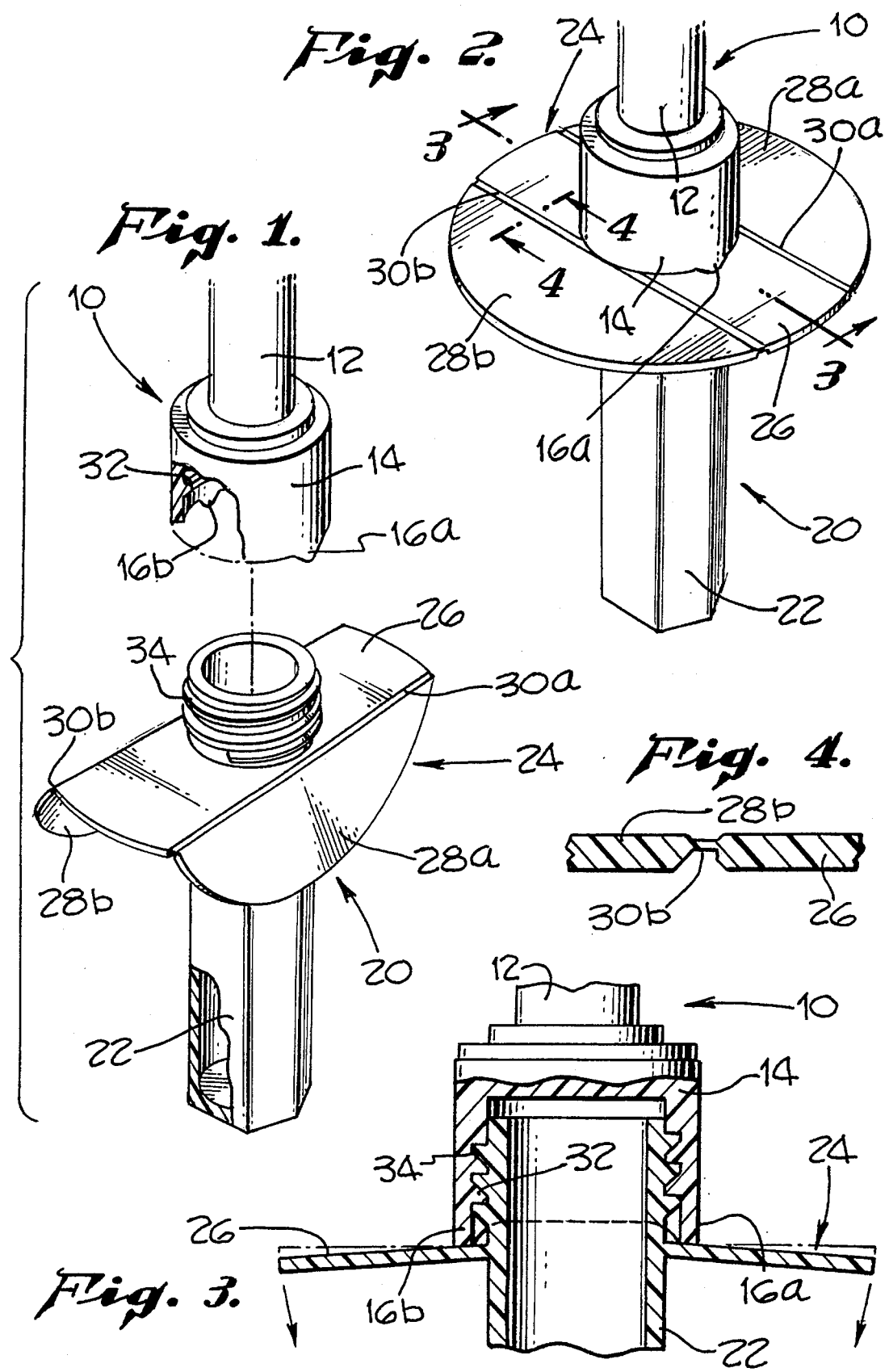

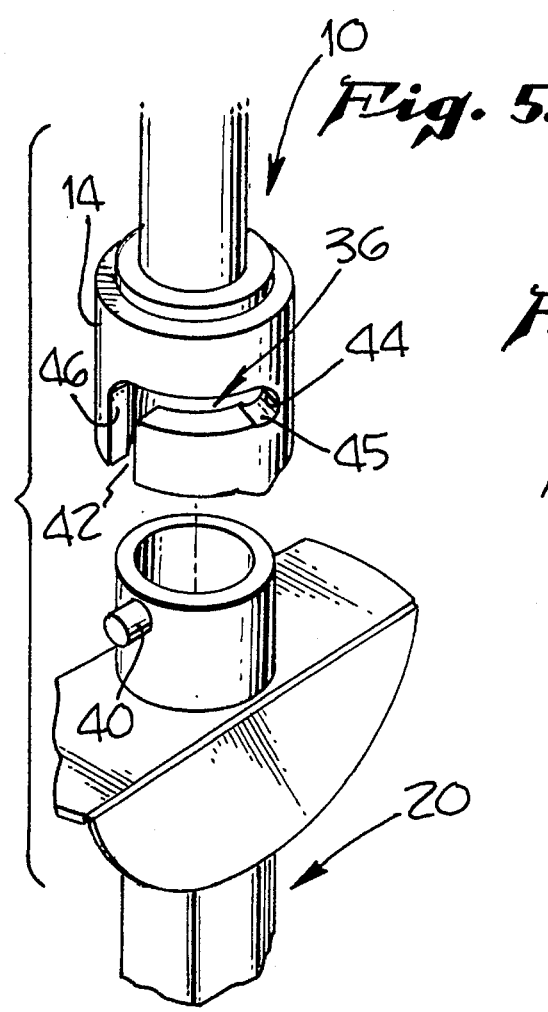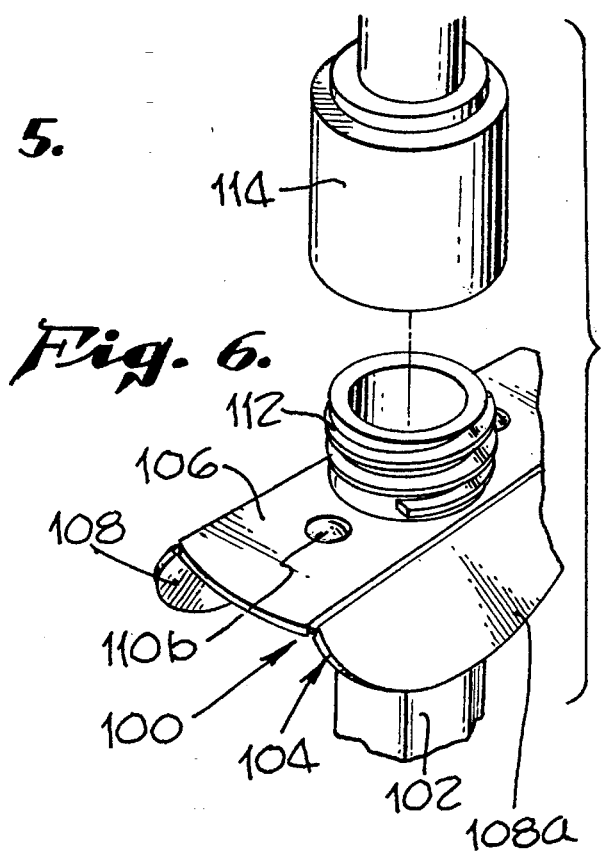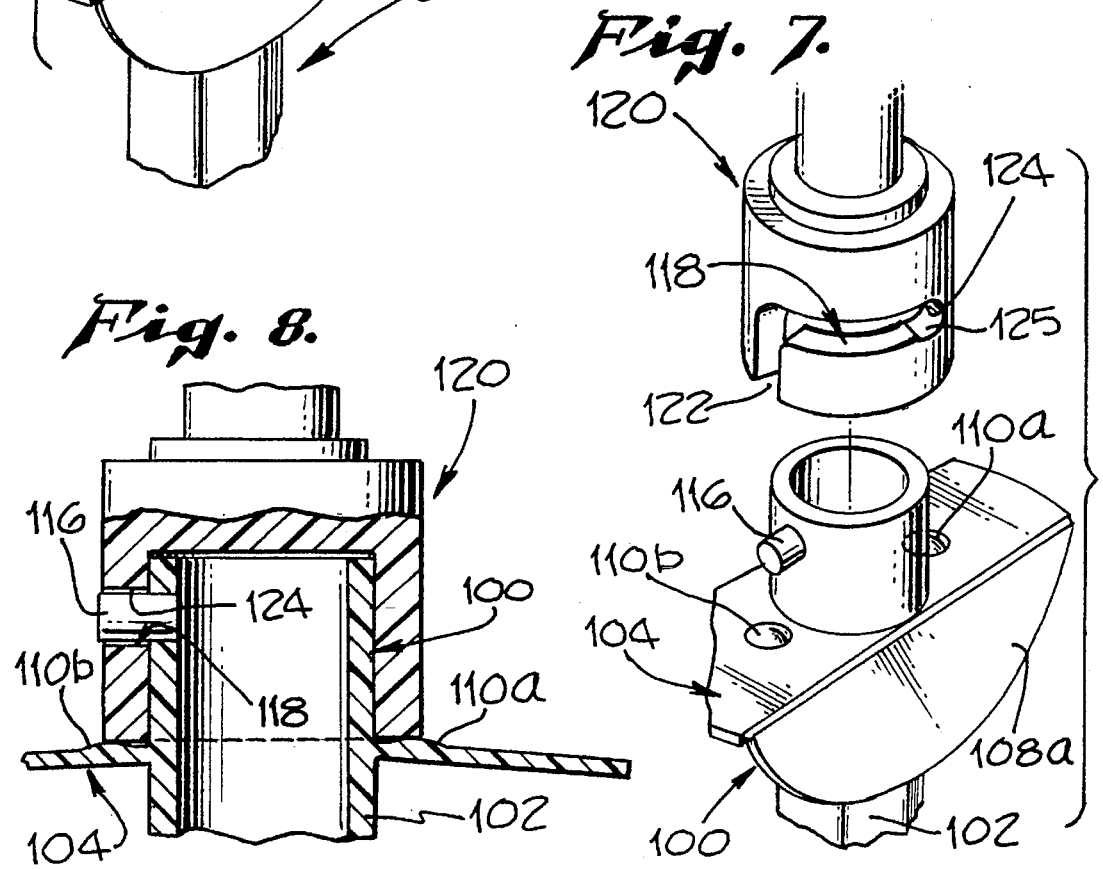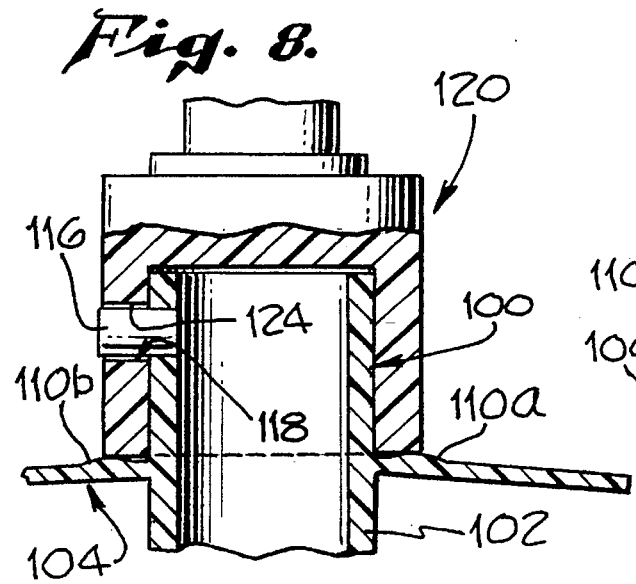

PROTECTIVE HANDLE AND ADAPTER FOR USE WITH A SURGICAL LIGHTING FIXTURE

BACKGROUND OF THE INVENTION

1. Field of Invention

The present invention relates generally to overhead surgical lighting fixtures and, more specifically, to disposable handles for use with surgical lighting fixtures.

2. Description of the Related Art

Generally, surgical lighting fixtures are composed of a mechanical suspension system and a main body which houses a number of electric lamps. The suspension system allows the lighting fixture to be moved horizontally, vertically and at various angles. As such, the lighting fixtures may be easily manipulated by operating room personnel in order to focus the light produced by the lamps on the appropriate location.

One common method of preventing contamination of sterile surgical environments is to provide disposable handles for surgical lighting fixtures. Such handles may include an elongate portion which is gripped during manipulation of the lighting fixture and a shield which extends radially from the elongate portion. The shield prevents the user's hand from extending beyond the elongate handle and contacting the lighting fixture. If the operating environment is of the type where the lighting fixture is a non-sterile element, then the handle prevents the contamination of gloves worn by those who adjust the fixture.

Disposable handles are often included in hermetically sealed "surgical kits" which include sterile sets of surgical instruments needed for a particular surgical procedure. Prior to surgery, operating room personnel simply open the kit and attach the disposable handle to the lighting fixture. During surgery, the only portion of the lighting fixture which is touched is the disposable handle. After surgery, the handle may be removed from the lighting fixture and discarded.

One disadvantage of prior art disposable handles is that, due to their radially extending shields, they cannot be arranged so that they lie flat. This makes it difficult to pack them in surgical kits which contain generally flat instruments such as scalpels, clamps and the like. U.S. Pat. No. 4,974,288 to Reasner provides an advantageous solution to this problem in the art. As illustrated in FIGS. 1–7 of the '288 patent, the Reasner shield includes a pair of hinged side portions which may be folded downwardly, thereby forming a compact device which may be easily packed in a surgical kit. After the surgical kit is opened, the hinged side portions may be manually repositioned from a folded orientation to the orientation shown in FIG. 3 of the '288 patent. The handle may then be screwed into an adapter socket which is attached to the lighting fixture.

OBJECT AND SUMMARY OF THE INVENTION

The general object of the present invention is to provide an improved disposable surgical handle and/or adapter system. More particularly, one object of the present invention is to provide a disposable surgical handle and/or adapter system which enables a user to attach a disposable handle having a shield with hinged side portions, such as that disclosed in the '288 patent, to an adapter without having to first unfold the hinged side portions.

In order to accomplish these and other objectives, the present invention may include biasing means, associated with at least one of an adapter and a shield, for biasing the shield in such a manner that if the side portions of the shield are arranged in the folded position, then the side portions will be repositioned to the use position when the handle and the adapter are secured to one another.

An adapter in accordance with a first preferred embodiment of the present invention may include a body portion, a fastening element associated with the body portion to secure a surgical handle (the surgical handle preferably being of the type having a shield composed of a central portion and a pair of side portions respectively hinged to opposite sides of the central portion) and a biasing element associated with the body and opposing the central portion of the shield in such a manner that the central portion of the shield is biased by the body when the handle is secured to the adapter. Thus, upon attachment of the handle to the adapter, the side portions to "spring" or "snap" into alignment with the central portion.

The first preferred embodiment of the present invention significantly advances the state of the art. More particularly, the first preferred embodiment allows surgical personnel to simply remove a handle from its container, or from a surgical kit, and fasten it to the surgical lighting fixture. The side portions do not have to be unfolded because they are unfolded by the adapter when the handle is fastened to the lighting fixture.

In accordance with a second preferred embodiment of the present invention, a surgical lighting fixture handle may include an elongate gripping member having a fastening element, a shield extending radially from the gripping member, the shield defining a central portion and a pair of side portions, and a biasing element associated with the shield. Upon attachment of the handle to an adapter on the surgical lighting fixture, the biasing element (and the central portion of the shield) is deflected. As noted above, such deflection causes the hinged side portions to "spring" or "snap" into alignment with the central portion, thereby eliminating the need for surgical personnel to unfold the end portions prior to installation.

BRIEF DESCRIPTION OF THE DRAWINGS

Detailed descriptions of preferred embodiments of the invention will be made with reference to the accompanying drawings.

FIG. 1 is a perspective view in accordance with a first preferred embodiment of the present invention.

FIG. 2 is a perspective view in accordance with the preferred embodiment illustrated in FIG. 1.

FIG. 3 is a section view taken along section line 3—3 in FIG. 2.

FIG. 4 is a section view taken along section line 4—4 in FIG. 2.

FIG. 5 is a perspective view in accordance with the first preferred embodiment of the present invention.

FIG. 6 is a perspective view in accordance with a second preferred embodiment of the present invention.

FIG. 7 is a perspective view in accordance with the second preferred embodiment of the present invention.

FIG. 8 is a section view of the preferred embodiment illustrated in FIG. 7.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention. The scope of the invention is defined by the appended claims.

A first preferred embodiment of the present invention is illustrated, for example, in FIG. 1. In accordance with the first preferred embodiment, an adapter 10 may include a stem 12 disposed on one end of a generally cylindrically shaped body portion 14. The stem 12 may have a smooth surface that can be affixed to a corresponding socket in a surgical lighting fixture by a suitable adhesive. Conversely, the stem 12 may be threaded so that it can be screwed into a threaded socket. The adapter also includes a biasing element. In the illustrated embodiment, the biasing element is composed of a pair of protrusions 16a and 16b which extend from the other end of the main body portion 12.

A disposable plastic handle 20, such as that illustrated in FIG. 1, may be secured to the adapter 10. Such handles generally include an elongate portion 22 which supports a shield 24. The shield 24 is composed of a central portion 26 and hinged side portions 28a and 28b. The side portions 28a and 28b are respectively connected to the central portion 26 by living hinges 30a and 30b (see FIG. 4). The shield 24 is flexible about the elongate portion 22.

The adapter 10 also includes a fastening element which cooperates with a corresponding element on the handle 20 to secure the handle in place. As illustrated for example in FIG. 1, the inner portion of the adapter 10 may include threads 32 which are adapted to engage threads 34 formed on the handle 20. The threads 32 are arranged such that the protrusions 16a and 16b will align with, and deflect, the central portion 26 of shield 24 when the handle 20 is screwed tightly into the adapter 10 as shown in FIGS. 2 and 3.

Referring for example to FIGS. 2 and 3, and as noted above, the side portions 28a and 28b are bent downwardly (in the orientation shown in FIG. 1) when they are unpacked. The central portion 26 is strait. However, when the central portion 26 of the shield 24 is deflected by the protrusions 16a and 16b of the adapter 10 in the manner illustrated in FIG. 3, the side portions 28a and 28b "spring" or "snap" into the position illustrated in FIG. 2. As such, the side portions 28a and 28b do not have to be repositioned prior to the attachment of the disposable handle to the surgical lighting fixture.

The fastening element is not limited to the threaded arrangement described above. As illustrated for example in FIG. 5, the fastening element may be composed of a generally L-shaped channel 36 formed in the main body portion 14. The disposable handle 20 used with such an adapter would include a detent or tab 40 which is adapted to engage the channel 36. The channel 36 includes an open end 42 and a closed end 44. The closed end includes a recess 45. Attachment of the disposable handle to the adapter is performed by inserting the handle into the adapter in such a manner that the detent 40 is aligned with the open end 42 of the channel 36. After the detent 40 reaches corner 46, the handle is rotated until the detent 40 reaches the closed end 44 and rests in the recess 45. The closed end 44 and the detent 40 are respectively positioned so that the protrusions 16a and 16b will deflect the central portion 26 of the shield 24. As noted above (and as illustrated in FIG. 2), such deflection causes the side portions 28a and 28b to "spring" or "snap" upwardly into alignment with the central portion 26.

The adapter may be formed from plastic materials such as acetal and Delrin. Alternatively, the adapter may be composed of stainless steel or other suitable materials known to those of skill in the art.

A second preferred embodiment of the present invention is illustrated, for example, in FIG. 6. In accordance with the second preferred embodiment, a handle 100 for use with a surgical lighting fixture may include an elongate gripping member 102 having a radially extending shield 104. The shield 104 is composed of a central portion 106 and a pair of side portions 108a and 108b respectively hinged to opposite sides of the central portion. A biasing element is associated with the shield. In the illustrated embodiment, the biasing element is composed of a pair of protrusions 110a and 110b which are arranged on the central portion 106. The handle 100 also includes a fastening element.

In the exemplary embodiment illustrated in FIG. 6, the fastening element consists of a thread arrangement 112 which may be engaged with a correspondingly threaded adapter 114 affixed to a surgical lighting fixture or to a thread arrangement formed in the surgical lighting fixture itself. The handle 100 may be screwed into the corresponding adapter or lighting fixture beyond the point at which the protrusions 110a and 110b first contact the adapter or lighting fixture, thereby deflecting the central portion 106 of the shield. Such deflection causes the side portions 108a and 108b to "spring" or "snap" into alignment with the central portion 106.

As discussed above with reference to FIG. 5, the present invention is not limited to a threaded fastening element. Numerous other means of fastening the handle 100 to an adapter or lighting fixture may be employed. One example of an alternate fastening element, a tab 116 formed on the handle 100 and adapted to engage a generally L-shaped channel 118 formed in an adapter 120, is illustrated in FIGS. 7 and 8. This operation of this arrangement is discussed above with reference to FIG. 3. Here, moving the tab 116 from an open end 122 of the channel 118 to a closed end 124 causes the protrusions 110a and 110b to be deflected by the adapter 120. Such deflection causes the side portions 108a and 108b to "spring" or "snap" into alignment with the central portion of the shield. The closed end 124 may include a recess 125 to prevent rotation of the handle.

The handle 100 may be molded from plastics such as polypropylene or polystyrene, which is more rigid than polypropylene, or other suitable materials known to those of skill in the art. The height of the protrusions 108a and 108b will vary with the rigidity of the material used to form the handle. The more rigid the material, the higher the protrusions must be.

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

We claim:

1. In a lighting fixture handle and adapter assembly for attaching a handle to a lighting fixture, the handle including an elongate member and a shield extending radially therefrom, the shield defining a central portion and two side portions respectively hinged to opposite sides of the central portion, the side portions being movable between a folded position and a use position in which the side portions are substantially aligned with the sides of the central portion, the improvement comprising:

biasing means, operably connected to at least one of the adapter and the shield, for biasing the shield in such a manner that if the side portions of the shield are arranged in the folded position, then the side portions will be repositioned to the use position when the handle and the adapter are secured to one another.

2. A lighting fixture handle and adapter assembly as claimed in claim 1, wherein the biasing means comprises at least one protrusion formed on at least one of the adapter and the central portion of the shield.

3. A lighting fixture handle and adapter assembly as claimed in claim 2, wherein the at least one protrusion is formed on the central portion of the shield.

4. A lighting fixture handle and adapter assembly as claimed in claim 3, wherein the central portion of the shield defines first and second ends separated by the elongate member, and said at least one protrusion comprises a first protrusion being formed on the first end and a second protrusion being formed on the second end.

5. A lighting fixture handle and adapter assembly as claimed in claim 2, wherein the at least one protrusion is formed on the adapter.

6. A lighting fixture handle and adapter assembly as claimed in claim 5, wherein the adapter defines a longitudinal free end and the at least one protrusion is formed on the longitudinal free end.

7. A lighting fixture handle and adapter assembly as claimed in claim 6, wherein a pair of protrusions are formed on the longitudinal free end of the adapter.

8. An adapter for connecting a handle to a surgical lighting fixture, the handle including an elongate member and a shield extending radially from the elongate member, the shield defining a central portion and two side portions respectively hinged to opposite sides of the central portion, the adapter comprising:

a generally cylindrically shaped body;

a fastening element operably connected to the body to secure the handle to the body; and a biasing element operably connected to said body and opposing said central portion of said shield in such a manner that the central portion of the shield is biased by the biasing element when said handle is secured to said adapter.

9. An adapter for connecting a handle to a surgical lighting fixture as claimed in claim 8, wherein the side portions of the shield are movable between a folded position and a use position in which the side portions are substantially aligned with the sides of the central portion of the shield, and wherein said biasing element is provided in association with said body in such a manner that the central portion is biased to position the shield side portions toward the use position when the handle and the adapter are secured to one another.

10. An adapter for connecting a handle to a surgical lighting fixture as claimed in claim 8, wherein the biasing element comprises at least one protrusion which biases the central portion of the shield when the handle and adapter are secured to one another.

11. An adapter for connecting a handle to a surgical lighting fixture as claimed in claim 10, wherein the fastening element comprises threads adapted to cooperate with a threaded portion of the handle, the threads of the fastening element being arranged such that said at least one protrusion is aligned with the central portion of the shield when the adapter and the handle are secured to one another.

12. An adapter for connecting a handle to a surgical lighting fixture as claimed in claim 8, further comprising a stem operably connected to the body and adapted to be secured to the surgical lighting fixture.

13. A handle for use with a surgical lighting fixture, the surgical lighting fixture including an adapter for receiving the handle, the handle comprising:

an elongate gripping member having a fastening element adapted to be secured to the adapter;

a shield extending radially from the gripping member, the shield including a central portion defining a surface and a pair of side portions respectively hinged to opposite sides of the central portion; and a biasing element operably connected to the surface of the shield;

wherein the biasing element biases the central portion of the shield when the handle and adapter are secured to one another.

14. A handle for use with a surgical lighting fixture as claimed in claim 13, wherein the side portions of the shield are movable between a folded position and a use position in which the side portions are substantially aligned with the sides of the central portion of the shield, and the biasing element biases the central portion in such a manner that if the side portions are arranged in the folded position, then the side portions will be repositioned to the use position when the handle and the adapter are secured to one another.

15. A handle for use with a surgical lighting fixture as claimed in claim 13, wherein the biasing element comprises at least one protrusion operably connected to the central portion of the shield.

16. A handle for use with a surgical lighting fixture as claimed in claim 15, wherein the fastening element is adapted to be inserted into the adapter, said at least one protrusion contacting the adapter when the handle is fully inserted into the adapter, thereby biasing the shield.

17. A handle for use with a surgical lighting fixture as claimed in claim 16, wherein the fastening element comprises threads adapted to cooperate with a threaded portion of the adapter.

* * * * *